(12) United States Patent
Barthelemy et al.

(10) Patent No.: US 10,343,934 B2
(45) Date of Patent: Jul. 9, 2019

(54) HYDROGEL-BASED DECONTAMINATION OF AQUEOUS SAMPLES CONTAINING NANOPARTICLES

(71) Applicant: UNIVERSITE DE BORDEAUX, Bordeaux (FR)

(72) Inventors: Philippe Barthelemy, Merignac (FR); Alain Thiery, Avignon (FR); Amit Patwa, Bordeaux (FR)

(73) Assignee: UNIVERSITE DE BORDEAUX, Bordeaux (FR)

( * ) Notice: Subject to any disclaimer, the term of this patent is extended or adjusted under 35 U.S.C. 154(b) by 881 days.

(21) Appl. No.: 14/374,676

(22) PCT Filed: Jan. 25, 2013

(86) PCT No.: PCT/FR2013/050163
§ 371 (c)(1),
(2) Date: Nov. 11, 2014

(87) PCT Pub. No.: WO2013/110902
PCT Pub. Date: Aug. 1, 2013

(65) Prior Publication Data
US 2015/0076062 A1    Mar. 19, 2015

(30) Foreign Application Priority Data
Jan. 25, 2012 (FR) .................................. 12 00233

(51) Int. Cl.
*C02F 1/26* (2006.01)
*B01D 15/08* (2006.01)
(Continued)

(52) U.S. Cl.
CPC ................ *C02F 1/26* (2013.01); *B01D 15/08* (2013.01); *C02F 1/285* (2013.01); *C02F 1/286* (2013.01);
(Continued)

(58) Field of Classification Search
CPC ............ C02F 1/26; C02F 1/286; C02F 1/285; C02F 2305/00; C07H 19/06; C07H 19/207;
(Continued)

(56) References Cited

U.S. PATENT DOCUMENTS

2008/0190860 A1* 8/2008 Franks ................... B01D 21/01
210/724

FOREIGN PATENT DOCUMENTS

| EP | 2502856 A1 | 9/2012 |
| JP | 2011104522 A | 6/2011 |
| WO | 2005116043 A1 | 12/2005 |

OTHER PUBLICATIONS

Xinqing Chen et al. "Precious metal recovery by selective absorption using biosorbents", Journal of Hazardous Materials, Elsevier, Nov. 22, 2011, vol. 186, No. 1, pp. 902-910.
(Continued)

*Primary Examiner* — Taiwo Oladapo
(74) *Attorney, Agent, or Firm* — Cantor Colburn LLP (57) ABSTRACT

The present invention relates to the use of a supramolecular system in order to remove particles from a liquid medium containing same. According to the invention, the supramolecular system includes at least one molecule having a low molecular weight and/or an organic compound from living organisms, preferably from jellyfish, said compound being selected from among collagen, a polysaccharide, a proteoglycan or a mixture of two of said organic compounds, and said molecule having a low molecular weight and formula (I) as defined herein. The invention also relates to a method for removing particles from a liquid medium containing same. The invention is particularly suitable for use in water decontamination and biotechnology.

11 Claims, 3 Drawing Sheets

(51) Int. Cl.
  *C02F 1/28* (2006.01)
  *C07H 19/10* (2006.01)
  *C07H 19/073* (2006.01)
  *C07H 19/20* (2006.01)
  *C07H 19/207* (2006.01)
  *C07H 19/06* (2006.01)

(52) U.S. Cl.
  CPC ........... *C07H 19/06* (2013.01); *C07H 19/073* (2013.01); *C07H 19/10* (2013.01); *C07H 19/20* (2013.01); *C07H 19/207* (2013.01); *C02F 2305/00* (2013.01); *Y02W 10/37* (2015.05)

(58) Field of Classification Search
  CPC ...... C07H 19/073; C07H 19/20; C07H 19/10; B01D 15/08; Y02W 10/37
  See application file for complete search history.

(56) References Cited

OTHER PUBLICATIONS

Sisir Debnath et al. "Dipeptide-Based Low-Molecular-Weight Efficient Organogelators and Their Application in Water Purification", Chemistry—A European Journal, Aug. 8, 2008, vol. 14, No. 23, pp. 6870-6881.

Guilhem Godeau et al. "Glycosyl-nucleoside fluorinated amphiphiles as components of nanostructured hydrogels", Tetrahedron Letters, Elsevier, Feb. 17, 2010, vol. 51, No. 7, 1012-1015.

Guilhem Godeau et al. "Glycosyl-Nucleoside Lipids as Low-Molecular-Weight Gelators" Langmuir Letter, Aug. 4, 2009, vol. 25, No. 15; pp. 8447-8450.

Guilhem Godeau et al. "Glycolsyl-nucleoside-lipid based supramolecular assembly as a nanostructured material with nucleic acid delivery capabilities", Chemical Communications, Jul. 17, 2009, No. 34, pp. 5127-5129.

Raziya Nadeem et al. "Fourier Transform Infrared Spectroscopic characterization and optimization of Pb(II) biosorption by fish (*Labeo rohita*) scales", Journal of Hazardous Materials, Elsevier, Aug. 15, 2008, vol. 156, No. 1-3, pp. 64-73.

Rongjun Qu et al. "Adsorption of Au(III) from aqueous solution using cotton fiber/chitosan composite adsorbents", Hydrometallurgy, Elsevier Scientific, Dec. 1, 2009, vol. 100, No. 1-2, pp. 65-71.

Maria E. Romero-Gonzalez et al. "Spectroscopic Studies of the Biosorption of Gold (III) by Dealginated Seaweed Waste", Environment Science & Technology, Sep. 1, 2003, vol. 37, No. 18, pp. 4163-4169.

Kondapalli Srividya et al. "Biosorption of hexavalent chromium form aqueous solutions by Catla catla scales: Equilibrium and kinetics studies", Chemical Engineering Journal, Elsevier, Dec. 15, 2009, vol. 155, No. 3, pp. 666-673.

L.S. Strizhko et al. "Extracting Noble Metals from Industrial Solutions and Waste Waters with Biosorbents", Russian Journal of Non-Ferrous Metals, Apr. 2, 2009, vol. 50, No. 2, pp. 118-122.

Yang Zhang et al. "Stability and Removal of Water Soluble CdTe Quantum Dots in Water", Environmental Science & Technology, Jan. 1, 2008, vol. 42, No. 1, pp. 321-325.

* cited by examiner

HYDROGEL-BASED DECONTAMINATION OF AQUEOUS SAMPLES CONTAINING NANOPARTICLES

RELATED APPLICATION

This application is a national stage entry of PCT/FR2013/050163, filed Jan. 25, 2013, which claims priority from France Patent Application No. 1200233, filed Jan. 25, 2012, which are incorporated by reference in their entirety.

TECHNICAL FIELD

The present invention relates to the use of a supramolecular system for subtracting particles from a liquid medium containing same, wherein said supramolecular system comprises at least one low-molecular-weight molecule and/or one organic compound from living organisms, preferably jellyfish, said compound being chosen from collagen, a polysaccharide, a proteoglycan or a mixture of two of these organic compounds, said low-molecular-weight molecule being of formula (I) as defined herein.

It also relates to a process for subtracting particles from a liquid medium containing same.

It is in particular of use in the water decontamination and biotechnology field.

In the description below, the references between square brackets ([ ]) refer to the list of references given at the end of the examples.

PRIOR ART

Numerous research studies have recently been carried out in the field of the decontamination of residual water, waste water, drinking water or, generally, any aqueous solutions used in particular for food or for industry.

Currently, the treatment of contaminated water consists of the use of physical processes for removing solid or particulate elements, of physicochemical treatments for removing decantable particulate matter or of biological treatments for removing organic matter.

Thus, numerous techniques have been developed for destroying or removing unwanted or toxic materials contained in soiled water. They are, for example, the exposure of water to ultraviolet (UV) radiation, the use of electrodes and of an electric current to capture charged molecules, the addition of coagulants, of flocculants or of chlorine, the use of microorganisms, etc.

Activated carbon can also be used, but the methods using this type of material prove to be expensive and require maintenance and considerable management.

The use of ozone ($O_3$) also constitutes a method of decontamination mainly for the oxidation of organic matter. However, this method requires complex equipment, used for treating large volumes. It is not therefore suitable for the decontamination of small volumes.

Consequently, it proves to be the case that the current decontamination methods are barely or not at all suitable for decontaminating liquid media polluted with particles, in particular small particles, for example nanoparticles. In addition, these methods are not necessarily suitable for decontaminating a liquid medium either on a large scale or in small volumes.

Nanofiltration and reverse osmosis processes are the methods currently used to remove nanoparticles from liquid media. However, these methods involve devices and implementations which are very expensive, and require a great deal of maintenance.

Moreover, numerous health concerns relating to possible human, animal or environmental toxicity of nanoparticles have come to light, in particular following the evaluation by the Afssap [French Health Product Safety Agency], published on Jun. 14, 2011, regarding nanoparticles is cosmetics.

It is therefore essential to develop new methods for treating liquid media which make it possible to solve these prior art problems, in particular to provide means for ridding liquid media of particles, in particular of nanoparticles, that they might contain. It is also essential to develop a process for decontaminating a liquid medium containing particles, in particular nanoparticles, which makes it possible to reduce costs and to improve the decontamination compared with the prior art methods.

SUMMARY OF THE INVENTION

The present invention precisely meets these needs by providing a means for decontaminating a liquid medium containing unwanted particles.

Thus, a subject of the present invention is in particular the use of a supramolecular system for subtracting particles from a liquid medium containing same, wherein said supramolecular system comprises at least one low-molecular-weight molecule and/or one polymer, said low-molecular-weight molecule being of formula (I), and/or at least one organic compound from living organisms, preferably jellyfish, said compound being chosen from collagen, a polysaccharide, a proteoglycan or a mixture of two of these organic compounds, defined above.

The inventors are in fact the very first to have noted that low-molecular-weight molecules of formula (I), defined below, and/or polymers chosen from the group comprising collagen, a polysaccharide, a proteoglycan and a mixture of at least two of these polymers, make it possible to subtract the particles from a liquid medium comprising same by trapping the latter with a supramolecular system that can be separated from said liquid medium.

A subject of the present invention is also a process for subtracting particles from a liquid medium containing same, comprising a step (a) of adding a supramolecular system to said liquid medium at a temperature of between 2 and 95° C., wherein the supramolecular system comprises at least one low-molecular-weight molecule and/or at least one organic compound from living organisms, preferably jellyfish, said compound being chosen from collagen, a polysaccharide, a proteoglycan or a mixture of two of these organic compounds, said low-molecular-weight molecule being of formula (I), defined below, said supramolecular system forming a gel on contact with the liquid medium, said gel capturing the particles contained in said liquid medium, and a step (b) of separating said liquid medium and said gel having captured said particles.

According to the invention, when the temperature of the liquid medium obtained in step (a) is below 50° C., the process may also comprise, before step (b), the following intermediate steps:

(a1) heating the medium obtained in step (a) to a temperature of between 50 and 95° C., and (a2) cooling the medium obtained in step (a1) to a temperature of between 2 and 50° C.

These steps (a1) and (a2) are not obligatory. However, they make it possible to very greatly increase the speed of formation of the gel and therefore the decontamination of the liquid medium.

The expression "subtract particles from a liquid medium comprising same" or "subtracting of particles from a liquid medium containing same" is herein intended to mean trapping, or capturing, particles present in a liquid medium and then removing them from said medium. According to the invention, the particles are trapped or captured by the supramolecular system, and are then removed from the liquid medium by separating the gel formed by the supramolecular system from the liquid medium. It may, for example, be a question of decontaminating a liquid medium comprising particles or of a decontamination of a liquid medium comprising particles.

The term "particle" is herein intended to mean an aggregate resulting from the association of organic and/or inorganic molecules via weak bonds (such as van der Waals bonds or hydrogen bonds) or else strong bonds (such as covalent bonds or ionic bonds). Consequently, the particles do not possess a molecular weight.

Thus, according to the invention, the term "particle" excludes molecules in solution, for example dyes or oligonucleotides in solution, since they have a molecular weight.

The term "nanoparticles" is herein intended to mean particles of nanometric size (or ultrafine particle), according to ISO standard TS/27687, which are an assembly of molecules of which at least one of the dimensions is on the nanometric scale. For example, a "nanoparticle" according to the invention can be defined, according to the abovementioned ISO standard, as being a nano-object of which the three dimensions are on the nanometric scale, i.e. particles of which the nominal diameter is less than approximately 100 nm, preferably between 0.5 nm and 100 nm.

The present invention is particularly effective for decontaminating a liquid medium contaminated with nanoparticles and/or microparticles, for example particles of which the size is between 0.5 nm and 5 µm, for example between 0.5 nm and 1 µm, for example between 0.5 nm and 500 nm, for example between 1 and 50 nm, for example between 5 and 20 nanometers.

Advantageously, the particles have a size of between 1 nm and 500 nm, for example between 1 nm and 400 nm, for example between 5 nm and 300 nm, for example between 5 nm and 200 nm. Preferably, the particles are nanoparticles, i.e. particles of which the size is between 5 nm and 150 nm, for example between 5 nm and 100 nm.

By way of example of particles, mention may be made of fluorescent semiconductor nanocrystals, gold particles, silver particles, $TiO_2$ particles, CeO particles and ZnO particles. They may, for example, be any particles or any nanoparticles present in cosmetic products such as sun creams, in care products such as deodorants, in renovation products such as paints, etc.

Fluorescent semiconductor nanocrystals ("QDs" or "quantum dots") are inorganic nanoparticles of nanometric size, of approximately 10 nm, having unique optical properties. They are soluble in water and prove to be of use as an alternative to organic fluorophores in certain biomedical and biotechnological applications. Consequently, liquid waste discharged by chemical industries and research institutes can often be contaminated with encapsulated QDs. The present invention in fact provides means for trapping or eliminating the QDs present in a liquid medium, in order to decontaminate this liquid medium in terms of these nanoparticles.

Gold nanoparticles (AuNPs) are inorganic compounds of nanometric size, less than 100 nm, with unique optical, electronic and molecular recognition properties, which are of use in a large variety of fields, in particular electron microscopy, electronics, nanotechnology and materials science. Consequently, the liquid waste discharged by chemical industries and research institutes can be polluted with AuNPs. The present invention in fact provides means for trapping or eliminating the AuNPs present in a liquid medium, in order to decontaminate this liquid medium in terms of these nanoparticles.

According to the invention, the liquid medium is chosen from the group comprising an aqueous medium, an organic solvent, an emulsion and a polyphase medium.

The term "aqueous medium" is herein intended to mean any mixture comprising at least one liquid and the solvent of which is water.

The term "organic solvent" is herein intended to mean any solvent comprising organic compounds. For example, the liquid medium may be an organic solvent chosen from the group comprising a hydrocarbon, an oxygen-containing solvent and a halogenated solvent.

For example, the hydrocarbon may be an aliphatic hydrocarbon, for example an alkane or an alkene, or an aromatic hydrocarbon, for example benzene, toluene or xylene.

The oxygen-containing solvent may be, for example, chosen from the group comprising ethanol, methanol, acetone, acetic acid, ethyl acetate, an ether and a glycol ether.

The halogenated solvent may be, for example, chosen from the group comprising perchloroethylene, trichloroethylene, dichloromethane, chloroform and tetrachloromethane.

The term "polyphase medium" is herein intended to mean a medium comprising at least two immiscible liquid substances. The polyphase medium may be, for example, a two-phase medium, i.e. a medium comprising two phases, it may for example be an emulsion.

The term "emulsion" is herein intended to mean any macroscopically homogeneous but microscopically heterogeneous mixture of two immiscible liquid substances. For example, it may be an emulsion of the water-in-oil type or an emulsion of the oil-in-water type.

For example, the liquid medium in accordance with the invention may be a fluorocarbon-based, hydrocarbon-based medium.

Preferably, the liquid medium in accordance with the invention is an aqueous medium.

In the present description, the examples of a "heterocyclic base" comprise a (monocyclic, bicyclic or tricyclic) heterocyclic group comprising from 5 to 14 ring members, preferably from 5 to 10 ring members, having, as ring member other than the carbon atoms, 1 to 4 heteroatoms chosen from the group consisting of a nitrogen atom, a sulfur atom and an oxygen atom.

In the present description, the examples of a "linear or branched $C_1$-$C_5$ alkyl chain" comprise methyl, ethyl, propyl, isopropyl, butyl, isobutyl, sec-butyl, tert-butyl, pentyl, isopentyl, neopentyl and tert-pentyl.

In the present description, the examples of a "linear or branched $C_2$-$C_{30}$ alkyl chain" comprise ethyl, propyl, isopropyl, butyl, isobutyl, sec-butyl, tert-butyl, pentyl, isopentyl, neopentyl, tert-pentyl, hexyl, heptyl, octyl, nonyl, decyl, undecyl, dodecyl, tridecyl, tetradecyl, pentadecyl, hexadecyl, heptadecyl, octadecyl, enneadecyl, eicosanyl, triacontanyl or an unsaturated group of oleyl, linoleyl, or linoleyl type.

In the present description, the term "heteroaryl comprising 1 to 4 nitrogen atoms" is intended to mean an aryl comprising from 1 to 4 heteroatoms, in particular chosen from the group comprising sulfur, oxygen, nitrogen and boron. By way of example of a heteroaryl comprising 1 to 4 nitrogen atoms, mention may be made of the following compounds: 1,2-diazole, 1,3-diazole, 1,4-diazole, 1,2,3-triazole, 1,2,4-triazole, 1,3,4-triazole, and tetrazoles.

In the present description, the examples of a "hydroxyalkyl chain" comprise saturated and unsaturated chains. By way of example of saturated $C_1$-$C_{19}$ hydroxyalkyl chains, mention may be made of hydroxyoctyl, hydroxynonyl, hydroxydecyl, hydroxydodecyl, hydroxytetradecyl, hydroxytetradecyl, hydroxypentadecyl, hydroxyhexadecyl, hydroxyheptadecyl, hydroxyoctadecyl and hydroxyenneadecyl chains.

In the present description, the examples of a "$C_2$-$C_{30}$ acyl chain" comprise ethyl, propyl, isopropyl, butyl, isobutyl, sec-butyl, tert-butyl, pentyl, isopentyl, neopentyl, tert-pentyl, hexyl, heptyl, octyl, nonyl, decyl, undecyl, dodecyl, tridecyl, tetradecyl, pentadecyl, hexadecyl, heptadecyl, octadecyl, enneadecyl, eicosanyl, triacontanyl or an unsaturated group of oleyl, linoleyl or linoleyl type.

In the present description, the examples of a "$C_2$-$C_{30}$ hydrocarbon-based chain" may be saturated or unsaturated and may be branched or unbranched. By way of example of a saturated $C_2$-$C_{30}$ hydroalkyl chain, mention may be made of octyl, nonyl, decyl, dodecyl, myristyl, palmityl and stearyl chains. By way of example of an unsaturated $C_2$-$C_{30}$ hydroalkyl chain, mention may be made of oleyl, linoleyl, linoleyl and arachidonyl chains.

In the present description, the examples of "$C_1$-$C_{19}$ hydrocarbon-based" may be saturated or unsaturated and may be branched or unbranched. By way of example of saturated $C_1$-$C_{19}$ hydroalkyl chains, mention may be made of octyl, nonyl, decyl, dodecyl, myristyl, palmityl and stearyl chains. By way of example of unsaturated $C_1$-$C_{19}$ hydroalkyl chains, mention may be made of oleyl, linoleyl and linoleyl chains.

In the present description, the examples of a "fluorocarbon-based chain" comprise from 1 to 30 carbon atoms and can be chosen from the group comprising trifluoromethyl, pentafluoroethyl, heptafluoropropyl, nonafluorobutyl, undecafluoropentyl, perfluorohexyl, perfluorooctyl, perfluorodecyl, perfluoroundecyl, perfluorododecyl, perfluoroundecyl and perfluorododecyl.

In the present description, the examples of a "hydrofluorocarbon-based chain" comprise from 1 to 30 carbon atoms and can be chosen from the group comprising 1H,1H,2H,2H-perfluoroheptyl, 1H,1H,2H,2H-perfluorooctyl, 1H,1H,2H,2H-perfluorononyl, 1H,1H,2H,2H-perfluorodecyl, 1H,1H,2H,2H-perfluoroundecyl, 1H,1H,2H,2H-perfluorododecyl, 7H,7H,7H,6H,6H-perfluoroheptyl, 8H,8H,8H,7H,7H-perfluorooctyl, 9H,9H,9H,8H,8H-perfluorononyl, 10H,10H,10H,9H,9H-perfluorodecyl, 11H,11H,11H,10H,10H-perfluoroundecyl, 12H,12H,12H,11H,11H-perfluorododecyl, 1H,1H,3H,3H,5H,5H,7H,7H,9H,9H,11H,11H-perfluorododecyl and 2H,2H,4H,4H,6H,6H,8H,8H,10H,10H,12H,12H-perfluorododecyl.

In the present description, the examples of a "monosaccharide" comprise dihydroxyacetone, glyceraldehyde, erythrulose, erythrose, threose, ribulose, xylulose, arabinose, lyxose, ribose, xylose, deoxyribose, fructose, psicose, sorbose, tagatose, allose, altrose, galactose, glucose, gulose, idose, mannose, talose, fucose, fuculose, pneumose, quinovose, rhamnose, glucoheptose, idoheptulose, mannoheptulose, sedoheptulose and taloheptulose. Preferably, the monosaccharide is a glucose or a galactose.

In the present description, the examples of a "polysaccharide" comprise cellobiose, gentiobiose, inulobiose, isomaltose, isomaltulose, kojibiose, lactose, lactulose, laminaribiose, leucrose, maltose, maltulose, melibiose, nigerose, robinose, rutinose, saccharose, sophorose, trehalose, trehalulose, turanose, erlose, fucosyllactose, gentianose, inulotriose, 1-kestose, 6-kestose, maltotriose, mannotriose, melezitose, neokestose, panose, raffinose and rhamninose.

According to the invention, the at least one low-molecular-weight molecule is of formula (I) below:

(I)

wherein:
X represents an oxygen atom, a sulfur atom or a methylene group;
B represents a puric or pyrimidic base, or a monocyclic or bicyclic heterocyclic base, which is unnatural, each ring of which comprises 4 to 7 ring members, and which is optionally substituted with an $R_3'$ group as defined below;
substituents $L_1$ and $L_2$:
are identical or different and represent:
(i) a hydrogen atom,
(ii) a hydroxyl group,
(iii) a heteroaryl group comprising 1 to 4 nitrogen atoms, unsubstituted or substituted with a saturated or unsaturated, linear or branched $C_2$-$C_{30}$ hydrocarbon-based chain,
(iv) a monosaccharide or a polysaccharide, or
(v) a group chosen from an oxycarbonyl group —O—C(O)—, a thiocarbamate group —O—C(S)—NH—, a carbonate group —O—C(O)—O—, a carbamate group —O—C(O)—NH—, an ether group —O—, a phosphate group and a phosphonate group, knowing that said $L_1$ group is substituted with an $R_1$ group and said $L_2$ group is substituted with an $R_2$ group, where $R_1$ and $R_2$, which may be identical or different, represent:
a linear or branched, saturated or unsaturated, partially fluorinated or perfluorinated, $C_2$-$C_{30}$, preferably $C_6$-$C_{25}$, more preferentially $C_8$-$C_{25}$, hydrocarbon-based chawherein is unsubstituted or substituted on the chain-end carbon with a fluorine atom or with a benzyl or naphthyl ester or ether,
a $C_2$-$C_{30}$ acyl radical, or
an acylglycerol, sphingosine or ceramide group,
or
form a ketal group of formula (II) below:

(II)

formula (II) in which $K_1$ and $K_2$ are identical or different and represent a saturated or unsaturated $C_1$-$C_{19}$ hydrocarbon-based chain, $R_3$ and $R_3'$
  represent, independently of one another:
  (i) a hydroxyl, amino, phosphate, phosphonate, phosphocholine, O-alkyl phosphocholine, thiophosphate, phosphonium, —[$NH_2$—$R_4$]$^+$, —[$NHR_4R_5$]$^+$ or —[$NR_4R_5R_6$]$^+$ group wherein $R_4$, $R_5$ and $R_6$, independently of one another, are identical or different and represent (a) a hydrogen atom, (b) a linear or branched $C_1$-$C_5$ alkyl chain, or (c) a linear or branched $C_1$-$C_5$ hydroxyalkyl chain,
  (ii) a linear or branched $C_2$-$C_{30}$ alkyl chain optionally substituted with at least one hydroxyl group,
  (iii) a cyclodextrin group,
  (iv) a —$(CH_2)_n$—V—$R_8$ group, wherein V represents an —O—, —S— or —NH— group, $R_8$ represents a $C_2$-$C_{30}$ alkyl, and n is an integer from 1 to 50,
  (v) a —V—C(O)—$R_8$ group, wherein V represents an —O—, —S— or —NH— group, and $R_8$ represents a $C_2$-$C_{30}$ alkyl,
  or
  (vi) a heteroaryl group containing from 1 to 4 nitrogen atoms, said heteroaryl group being unsubstituted or substituted with a $C_2$-$C_{30}$ alkyl, or with a —$(CH_2)_n$—O—$(CH_2)_p$—$R_9$ group, or with a —$(CH_2)_{0-1}$—Y—C(=O)—R" group, or with a monosaccharide or polysaccharide, or with a group or with a group:

wherein:
  m is an integer from 1 to 6,
  p is an integer from 0 to 10 and
  $R_9$ represents a $C_1$ to $C_{10}$ alkyl group, or a cyclic ketal group containing 5 to 7 carbon atoms, said cyclic ketal group being unsubstituted or substituted with at least one linear or branched $C_2$-$C_{30}$ alkyl, a sterol group, a diacyl glycerol, a hydrofluorocarbon-based chain or at least one monosaccharide or polysaccharide,
  Y is an oxygen atom, an NH group or a sulfur atom,
  and R" is a hydrocarbon-based chain or a fluorocarbon-based chain,
  R' is a hydrocarbon-based chain, or
  are linked, independently of one another, via a covalent bond to another substituent $R_3$ or $R_3'$, which may be identical or different, of another compound of formula (I), which may be identical or different, so as to form a compound in dimer form.

The unnatural puric or pyrimidic bases can herein encompass the base:

wherein:
  $R_3'$ is as previously defined.

The phosphocholine group herein has the formula below:

The sterol group as previously defined can herein be, for example, a cholesteryl radical.

For example, the organic compound may be a polymer.

According to the invention, the at least one low-molecular-weight molecule is of formula (I) below:

(I)

wherein:
  X represents an oxygen atom, a sulfur atom or a methylene group;
  B represents a puric or pyrimidic base, or a monocyclic or bicyclic heterocyclic base, which is unnatural, each ring of which comprises 4 to 7 ring members, and which is optionally substituted with an $R_3$ group as defined below;
  substituents $L_1$ and $L_2$:
    are identical or different and represent:
      (i) a hydrogen atom,
      (ii) a hydroxyl group,
      (iii) a heteroaryl group comprising 1 to 4 nitrogen atoms, unsubstituted or substituted with a saturated or unsaturated, linear or branched $C_2$-$C_{30}$ hydrocarbon-based chain,
      (iv) a monosaccharide or a polysaccharide, or
      (v) a group chosen from an oxycarbonyl group —O—C(O)—, a thiocarbamate group —O—C(S)—NH—, a carbonate group —O—C(O)—O—, a carbamate group —O—C(O)—NH—, an ether group —O—, a phosphate group and a phosphonate group, knowing that said $L_1$ group is substituted with an $R_1$ group and said $L_2$ group is substituted with an $R_2$ group, where $R_1$ and $R_2$, which may be identical or different, represent:
  a linear or branched, saturated or unsaturated, partially fluorinated or perfluorinated, $C_2$-$C_{20}$, preferably $C_6$-$C_{25}$, more preferentially $C_8$-$C_{25}$, hydrocarbon-based chawherein is unsubstituted or substituted on the chain-end carbon with a fluorine atom or with a benzyl or naphthyl ester or ether,
  a $C_2$-$C_{20}$ acyl radical, or
  an acylglycerol, sphingosine or ceramide group,
or
  form a ketal group of formula (II) below:

(II)

wherein formula (II) $K_1$ and $K_2$ are identical or different and represent a saturated or unsaturated $C_1$-$C_{19}$ hydrocarbon-based chain,
$R_3$
  represents:
    (i) a hydroxyl, amino, phosphate, phosphonate, phosphocholine, O-alkyl phosphocholine, thiophosphate, phosphonium, —$NH_2$—$R_4$, —$NHR_4R_5$ or —$NR_4R_5R_6$ group wherein $R_4$, $R_5$ and $R_6$, independently of one another, are identical or different and represent (a) a hydrogen atom, (b) a linear or branched $C_1$-$C_5$ alkyl chain, or (c) a linear or branched $C_1$-$C_5$ hydroxyalkyl chain,
    (ii) a linear or branched $C_2$-$C_{30}$ alkyl chain optionally substituted with at least one hydroxyl group,
    (iii) a cyclodextrin group,
    (iv) a —$(CH_2)_n$—V—$R_8$ group, wherein V represents an —O—, —S— or —NH— group, $R_8$ represents a $C_2$-$C_{30}$ alkyl, and n is an integer from 1 to 50,
    (v) a —V—C(O)—$R_8$ group, wherein V represents an —O—, —S— or —NH— group, and $R_8$ represents a $C_2$-$C_{30}$ alkyl,
    or
    (vi) a heteroaryl group containing from 1 to 4 nitrogen atoms, said heteroaryl group being unsubstituted or substituted with a $C_2$-$C_{30}$ alkyl, or with a —$(CH_2)_m$—O—$(CH_2)_p$—$R_9$ group,
    wherein:
      m is an integer from 1 to 6,
      p is an integer from 0 to 10 and
      $R_9$ represents a cyclic ketal group containing 5 to 7 carbon atoms, said cyclic ketal group being unsubstituted or substituted with at least one linear or branched $C_2$-$C_{30}$ alkyl, a sterol group, a diacyl glycerol, a hydrofluorocarbon-based chain or at least one monosaccharide or polysaccharide,
or
  is linked, via a covalent bond, to another substituent $R_3$, which may be identical or different, of another compound of formula (I), which may be identical or different, so as to form a compound in dimer form.

Preferably, in formula (I):
X represents an oxygen atom or a methylene group, preferably an oxygen atom,
B represents a natural or unnatural puric or pyrimidic base, optionally substituted with an $R_3'$ group as defined below;
substituents $L_1$ and $L_2$:
  are identical or different and represent:
    (i) a hydrogen atom,
    (ii) a hydroxyl group,
    (iii) a heteroaryl group comprising 1 to 4 nitrogen atoms, unsubstituted or substituted with a saturated or unsaturated, linear or branched $C_2$-$C_{30}$ hydrocarbon-based chain,
    (iv) a group chosen from an oxycarbonyl group —O—C(O)—, a thiocarbamate group —O—C(S)—NH—, a carbonate group —O—C(O)—O—, a carbamate group —O—C(O)—NH—, an ether group —O—, a phosphate group or a phosphonate group, knowing that said $L_1$ group is substituted with an $R_1$ group and said $L_2$ group is substituted with an $R_2$ group, where $R_1$ and $R_2$, which may be identical or different, represent:
      a linear or branched, saturated or unsaturated, partially fluorinated or perfluorinated, $C_2$-$C_{30}$, preferably $C_6$-$C_{25}$, more preferentially $C_8$-$C_{25}$, hydrocarbon-based chain,
      a $C_2$-$C_{30}$ acyl radical, or
      an acylglycerol group,
    or
      form a ketal group of formula (II) below:

(II)

formula (II) in which $K_1$ and $K_2$ are identical or different and represent a saturated or unsaturated $C_1$-$C_{19}$ hydrocarbon-based chain,
$R_3$ and $R_3'$
  represent, independently of one another:
    (i) a hydroxyl, amino, phosphate, phosphonate, phosphocholine, O-alkyl phosphocholine, thiophosphate or phosphonium group,
    (ii) a linear or branched $C_2$-$C_{30}$ alkyl chain optionally substituted with at least one hydroxyl group,
    (iii) a —$(CH_2)_n$—V—$R_8$ group, wherein V represents an —O—, —S— or —NH— group, $R_8$ represents a $C_2$-$C_{30}$ alkyl, and n is an integer from 1 to 50,
    (iv) a —V—C(O)—$R_8$ group, wherein V represents an —O—, —S— or —NH— group, and $R_8$ represents a $C_2$-$C_{30}$ alkyl,
    or
    (v) a heteroaryl group containing from 1 to 4 nitrogen atoms, said heteroaryl group being unsubstituted or substituted with a $C_2$-$C_{30}$ alkyl, or with a —$(CH_2)_m$—O—$(CH_2)_p$—$R_9$ group, or with a —$(CH_2)_{0-1}$—Y—C(=O)$_p$—$R_9$ group, or with a monosaccharide or polysaccharide, or with a group:

or with a group:

wherein:

m is an integer from 1 to 6, p is an integer from 0 to 10 and $R_9$ represents a $C_1$ to $C_{10}$ alkyl group, or a cyclic ketal group containing 5 to 7 carbon atoms, said cyclic ketal group being unsubstituted or substituted with at least one linear or branched $C_2$-$C_{30}$ alkyl, a sterol group, a diacyl glycerol, a hydrofluorocarbon-based chain or at least one monosaccharide or polysaccharide, Y is an oxygen atom, an NH group or a sulfur atom, and R" is a hydrocarbon-based chain or a fluorocarbon-based chain, R' is a hydrocarbon-based chain, or are linked, independently of one another, via a covalent bond to another substituent $R_3$ or $R_3'$, which may be identical or different, of another compound of formula (I), which may be identical or different, so as to form a compound in dimer form.

For example, according to the invention, in formula (I) above,

X represents an oxygen atom, and/or

B represents a thymine, adenine, guanine, cytosine, 6-methoxypurine or hypoxanthine or a puric or pyrimidic base, which is unnatural, which can encompass:

wherein:

$R_3'$ is as defined below, and/or $L_1$ represents a hydroxyl group, $L_2$ represents a hydrogen atom, or $L_1$ and $L_2$ together form a ketal group of formula (II) below:

(II)

wherein $K_1$ and $K_2$ are identical or different and represent a saturated or unsaturated $C_1$-$C_{19}$ hydrocarbon-based chain and/or $R_3$ and $R_3'$ represent:

(i) a hydroxyl, amino, phosphate, phosphonate, phosphocholine, O-alkyl phosphocholine, thiophosphate or phosphonium group,

(ii) a linear or branched $C_2$-$C_{30}$ alkyl chain, optionally substituted with at least one hydroxyl group, (iii) a —$(CH_2)_n$—V—$R_8$ group, wherein V represents an —O—, —S— or —NH— group, $R_8$ represents a $C_2$-$C_{30}$ alkyl, and n is an integer from 1 to 50, (iv) a —V—C(O)—$R_8$ group, wherein V represents an —O—, —S— or —NH— group, and $R_8$ represents a $C_2$-$C_{30}$ alkyl, or (v) a heteroaryl group containing from 1 to 4 nitrogen atoms, said heteroaryl group being unsubstituted or substituted with a $C_2$-$C_{30}$ alkyl, or with a $(CH_2)_m$—O—$(CH_2)_p$—$R_9$ group, or with a —$(CH_2)_{0-1}$—Y—C(=O)$_p$—R" group, or with a monosaccharide or polysaccharide, or with a group:

or with a group:

wherein:

m is an integer from 1 to 6, p is an integer from 0 to 10 and $R_9$ represents a $C_1$ to $C_{10}$ alkyl group, or a cyclic ketal group containing 5 to 7 carbon atoms, said cyclic ketal group being unsubstituted or substituted with at least one linear or branched $C_2$-$C_{30}$ alkyl, a sterol group, a diacyl glycerol, a hydrofluorocarbon-based chain or at least one monosaccharide or polysaccharide, Y is an oxygen atom, an NH group or a sulfur atom, and R" is a hydrocarbon-based chain or a fluorocarbon-based chain,

R' is a hydrocarbon-based chain, or
are linked, independently of one another, via a covalent bond to another substituent $R_3$ or $R_3'$, which may be identical or different, of another compound of formula (I), which may be identical or different, so as to form a compound in dimer form.

According to the invention, in formula (I) above:
X represents an oxygen atom,
B represents an unnatural pyrimidic base substituted with a heteroaryl group containing three nitrogen atoms, said heteroaryl group being substituted with a group:

substituents $L_1$ and $L_2$ are identical or different and represent:
(i) a hydrogen atom,
(ii) a hydroxyl group,
$R_3$
represents a heteroaryl group comprising three nitrogen atoms, said heteroaryl group being substituted with a group:

or:

wherein:
R' is a hydrocarbon-based chain;
Y is an oxygen atom, an NH group or a sulfur atom, and R" is a hydrocarbon-based chain or a fluorocarbon-based chain,
or
is linked to another substituent $R_3$, which may be identical or different, of another compound of formula (I), which may be identical or different, so as to form a compound in dimer form.

According to the invention, in formula (I) above,
X represents an oxygen atom;
B represents a puric or pyrimidic base;
substituents $L_1$ and $L_2$ form a ketal group of formula (II) below:

wherein $K_1$ and $K_2$ are identical or different and represent a saturated or unsaturated $C_1$-$C_{19}$ hydrocarbon-based chain,
$R_3$
represents a phosphocholine group
or
is linked to another substituent $R_3$, which may be identical or different, of another compound of formula (I), which may be identical or different, so as to form a compound in dimer form.

Preferably, X represents herein an oxygen atom.

For example, in formula (I) above, the unnatural puric, pyrimidic or heterocyclic base may be substituted with at least one substituent chosen from a halogen and an amino, carboxy, carbonyl, carbonylamino, hydroxyl, azido, cyano, alkyl, cycloalkyl, perfluoroalkyl, alkyloxy, oxycarbonyl, vinyl, ethynyl, propynyl or acyl group.

Advantageously, a low-molecular-weight molecule in accordance with the invention has a molecular weight of between 400 Da and 5000 kDa.

For example, according to the invention, the at least one low-molecular-weight molecule may be an amphiphilic glycosyl nucleoside, for example an amphiphilic fluorinated glycosyl nucleoside ("FGN").

For example, the at least one low-molecular-weight molecule can be chosen from:
the group defined by formula (III) below, wherein R' is a hydrocarbon-based chain:

the group defined by formula (IV) below, wherein Y is an oxygen atom, an NH group or a sulfur atom, and R" is a hydrocarbon-based chain or a fluorocarbon-based chain:

the group defined by formula (V) below, wherein n is an integer between 0 and 19:

(V)

or the group defined by formula (VI) below, wherein n is an integer between 0 and 19:

(VI)

Preferably, the at least one low-molecular-weight molecule can be chosen from the group comprising:

5'-(4-((2H,2H,3H,3H-perfluoroundecanamide)methyl)-1H-1,2,3-triazol-1-yl)-N3-(1-((β-D-glucopyranoside)-1H-1,2,3,-triazol-4-yl)methyl)thymidine, 5'-(4-((1H,1H,2H,2H-perfluoroundecanamide)methyl)-1H-1,2,3-triazol-1-yl)-N3-(1-((β-D-glucopyranoside)-1H-1,2,3-triazol-4-yl)methyl)thymidine, 5'-(4-((oleamide)methyl)-1H-1,2,3-triazol-1-yl)-N3-(1-((β-D-glucopyranoside)-1H,1,2,3-triazol-4-yl)methyl)thymidine, 5'-(4-((stearamide)methyl)-1H-1,2,3-triazol-1-yl)-N3-(1-((β-D-glucopyranoside)-1H-1,2,3-triazol-4-yl)methyl)thymidine, 5'-(4-((octadecyloxy)methyl)-1H-1,2,3-triazol-1-yl)-N3-(1-((β-D-glucopyranoside)-1H-1,2,3-triazol-4-yl)methyl)thymidine, and 5'-(4-((cholesteryloxy)methyl)-1H-1,2,3-triazol-1-yl)-N3-(1-((β-D-glucopyranoside)-1H-1,2,3-triazol-4-yl)methyl)thymidine, 2',3'-O-18-pentatriacontanylidenuridine-5'-phosphocholine, 2',3'-O-18-pentatriacontanylidenadenosine-5'-phosphocholine, and a mixture of at least two of these compounds.

More preferably, the at least one low-molecular-weight molecule can be chosen from the group comprising:

5'-(4-((2H,2H,3H,3H-perfluoroundecanamide)methyl)-1H-1,2,3-triazol-1-yl)-N3-(1-((β-D-glucopyranoside)-1H-1,2,3-triazol-4-yl)methyl)thymidine.

Processes for producing such low-molecular-weight molecules are described, for example, in document WO 2005/116043 [1].

The supramolecular system according to the invention may comprise a polymer.

According to the invention, the term "polymer" is intended to mean any high-molecular-weight molecule consisting of monomers joined together via covalent bonds.

According to the invention, the polymer is chosen from the group comprising collagen, a polysaccharide, a proteoglycan, a glycosaminoglycan (GAG) and the mixture of at least two of these polymers.

For example, the polymer may be a synthetic polymer chosen from the group comprising polypeptides, polysaccharides and polynucleotides.

When the polymer is collagen, it may be chosen from the group comprising type I collagen, type II collagen and partially hydrolyzed collagen. For example, the partially hydrolyzed collagen may be gelatin.

When the polymer is a polysaccharide, it may be chosen from the group comprising amylopectin, amylose, dextrin, cyclodextrins, agar-agar, carrageenan, chitin, xylans, inulin, chitosan derivatives, starch and cellulose.

When the polymer is a proteoglycan, it may be chosen from the group comprising versican, perlecan, neurocan, aggrecan and fibroglycan.

Preferably, the polymer is a glycosaminoglycan (GAG). A glycosaminoglycan is a linear, i.e. unbranched, polysaccharide chain consisting of a repetition of disaccharide units. The disaccharide unit consists of a hexose or a hexuronic acid, linked to a hexosamine. The term "hexosamine" is intended to mean a sugar containing six carbon atoms, comprising an amine group.

When the polymer is a glycosaminoglycan (GAG; or a mucopolysaccharide (MPS)), it can be chosen from the group comprising heparin, sodium hyaluronate, keratan sulfate, heparan sulfate, chondroitin sulfate and dermatan sulfate.

According to the invention, the polymer may be a natural or synthetic polymer.

For example, the natural polymer may be a polymer originating from an invertebrate or vertebrate organism.

For example, the natural polymer may be a natural polymer originating from an invertebrate organism chosen from the group comprising jellyfish jelly and jelly plankton coating. For example, the jellyfish jelly is the jelly of the ctenophore *Mnemiopsis*. For example the jelly plankton coating is the coating of *Asplanchna*.

The jellyfish jelly and the jelly plankton coating consist of glycosaminoglycans (GAGs) and mucopolysaccharides (MPSs).

The mesoglea is capable of trapping nanoparticles after the death of the jellyfish. The capturing of the nanoparticles can be effective only when the mesoglea (gel) is brought into contact with the contaminated aqueous medium.

According to the invention, the concentration of the supramolecular system used, i.e. the concentration used of high-molecular-weight molecule and/or of polymer defined above, is between 0.001 mg·ml$^{-1}$ and 100 mg·ml$^{-1}$ of aqueous medium. For example, this concentration may be between 0.005 mg·ml$^{-1}$ and 50 mg·ml$^{-1}$, for example between 0.01 mg·ml$^{-1}$ and 20 mg·ml$^{-1}$, for example 10 mg·ml$^{-1}$.

A subject of the present invention is also a group of compounds of formula (IV) below:

wherein Y is an oxygen atom, and R" is a hydrocarbon-based chain or a fluorocarbon-based chain.

The hydrocarbon-based chain and the fluorocarbon-based chain are as defined above.

Processes for producing such low-molecular-weight molecules are described, for example, in document WO 2005/116043 [1].

Other advantages may become further apparent to those skilled in the art on reading the examples below, illustrated by the appended figures, given by way of nonlimiting illustration.

EXAMPLES

The purpose of the experiments presented below is to demonstrate that the supramolecular system used according to the invention makes it possible to decontaminate a liquid medium contaminated with particles.

Example 1: Decontamination of a Liquid Medium Containing QDs

In this example, FGNs (amphiphilic fluorinated glycosyl nucleosides) were used as supramolecular system comprising low-molecular-weight molecules for decontaminating a liquid medium comprising encapsulated quantum dots ("QDs").

Material

Amphiphilic Fluorinated Glycosyl Nucleosides (FGNs):
5'-(4-))2H,2H,3H,3H-Perfluoroundecanamide)methyl)-1H-1,2,3-triazol-1-yl)N3-)1-((b-D-glucopyranoside)-1H-1,2,3-triazol-4-yl)methylthymidine was synthesized according to the protocol described in the document Godeau et al. (Godeau et al., Tetrahedron Lett., 2010, vol. 51, p. 1012-1015 [2]).

Quantum Dots (QDs):
The QDs were obtained from the company Evident Technologies (catalog reference: ED-C11-TOL-0620). These QDs are at a concentration of 10 mg·ml$^{-1}$ in toluene (24.4 nM). Their core is composed of CdSe and their shell of ZnS. These QDs are encapsulated in trioctylphosphine oxide (TOPO).

The "QDs" have unique optical properties. Indeed, QDs of the same material, but having different sizes, can emit light of various colors. The physical reason is the quantum confinement effect.

DOPC:
The (2-{[(2S)-2,3-bis[(9Z)-octadec-9-enoyloxy]propyl-phosphonato]oxy}ethyl)trimethylazanium) was obtained from the company Genzyme Pharmaceuticals (catalog reference: LP-R4-070).

DOTAU:
The (N-[5'-(2',3'-dioleoyl)uridine]-N',N',N'-trimethylammonium tosylate) was synthesized according to the protocol described in the document Chabaud et al. (Chabaud et al., Bioconjugate Chem., 2006, vol. 17, p. 466-472 [3]).

Process for Encapsulating QDs in DOTAU/DOPC Micelles

200 µl of QDs encapsulated in TOPO (10 mg·ml$^{-1}$ in toluene) and 100 ml of chloroform were poured into an RB flask. The solvents were evaporated off in a rotary evaporator at 30° C. and then the QDs were dried under a high vacuum using a vacuum pump for 3 to 4 hours.

The QDs were then suspended in 35 ml of chloroform with 5 ml of phospholipids (2.5 ml DOTU and 2.5 ml DOPC, at a concentration of 10 mg·ml$^{-1}$ in chloroform).

400 µl of the solution obtained were then distributed into 100 test tubes (400 µl per tube). After complete evaporation of the chloroform from each test tube, the residues were heated to 80° C. and 1 ml of water was added to 50 of these test tubes in order to obtain a clear suspension containing DOTU/DOPC micelles. The content of each of these 50 test tubes was transferred into another of the other 50 test tubes in order to obtain an optically clear suspension containing DOTU/DOPC micelles. This transfer was carried out so as not to have a total volume greater than 50 ml.

The phospholipid-encapsulated QDs were then transferred into 2000 µl microtubes. Any aggregates of QDs encapsulated in the phospholipids were removed by centrifugation at 40000 rpm at 20-25° C. for twice 15 minutes.

In order to separate the QD solution from the residual aggregates, the supernatant was collected and transferred into a Vivaspin (cut-off threshold Mw of 30 kDa).

The total volume of the QD solution was reduced by 20 to 25 ml by centrifugation at 4000 rpm at 20-25° C. for 15 minutes. All the QD solution was then harvested in a flask and stored in the dark at 4° C.

The size of the encapsulated QDs obtained was less than or equal to 20 nm (measured on a Zetasizer apparatus by means of DLS experiments) (Binil Itty Ipe et al., *ChemPhysChem*, 2006, 7, 1112-1118 [4]).

Their concentration was 17 microg·ml$^{-1}$ in water (measured by fluorescence spectroscopy). The fluorescence spectra were recorded on an LS 55 spectrofluorimeter (Perkin Elmer) equipped with a xenon flashlamp. The data processing was carried out with the SigmaPlot 11 program.

Experimental Section: Formation of a Gel for Decontaminating a Solution Containing QDs 0.1 mg of FGNs in solution at 0.1% (i.e. 1.0 mg·ml$^{-1}$) was mixed with 1 ml of QDs in solution in water at a concentration of 17 μg·ml$^{-1}$ in a 2 ml microtube, at 20-25° C.

A gel was prepared by heating the solution to 80° C. in a water bath with constant agitation until a visually clear solution was obtained. The agitation time in this experiment was 3 to 4 minutes. The solution was then left in the dark for 48 hours in order for it to be able to stabilize.

Figure 1:
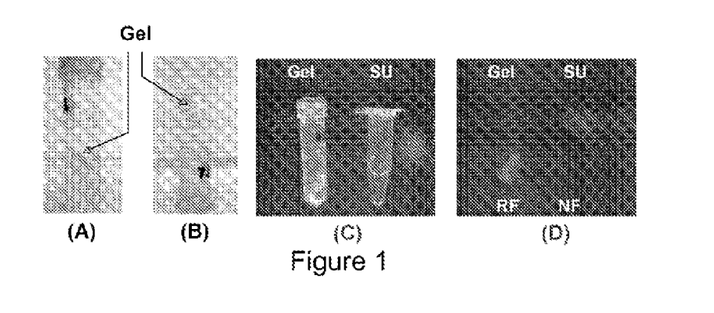
FIG. 1 represents a microtube comprising a hydrogel and a supernatant of a solution of encapsulated QDs. Represented in 1A is the microtube in the normal position. Represented in 1B is the same microtube as 1A in the upside down position. Represented in 1C is the hydrogel and the supernatant without UV. Represented in 1D is the same microtube as 1C under UV at $\lambda_{max}=312$ nm. "SU" means supernatant, "RF" means that a red fluorescence is observed, and "NF" means that no fluorescence is observed.

After 48 hours, a gel was formed with a liquid supernatant. The presence of the gel and of the supernatant was confirmed by turning the microtube upside down: the gel is maintained in the bottom of the tube, while the supernatant flows (see FIGS. 1A and 1B).

The liquid supernatant was separated from the gel. An observation of the liquid supernatant under UV ($\lambda_{max}$=312 nm) then confirmed that the encapsulated QDs were all captured by the gel. Indeed, a red fluorescence was observed for the gel, whereas no fluorescence was observed for the supernatant (FIGS. 1C and 1D).

Figure 2:
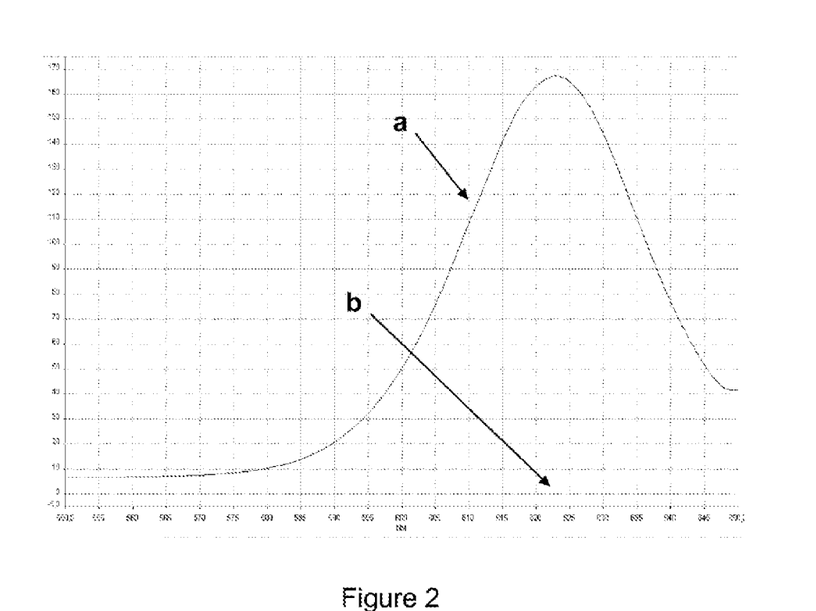
FIG. 2 represents a fluorescence spectrum of a solution of encapsulated QDs in water (a) and of the supernatant after the formation of the hydrogel according to the protocol described in this example (b). Represented along the x-axis is the wavelength in nanometers (NM) and represented along the y-axis is the intensity in arbitrary units (I).
Figure 3:
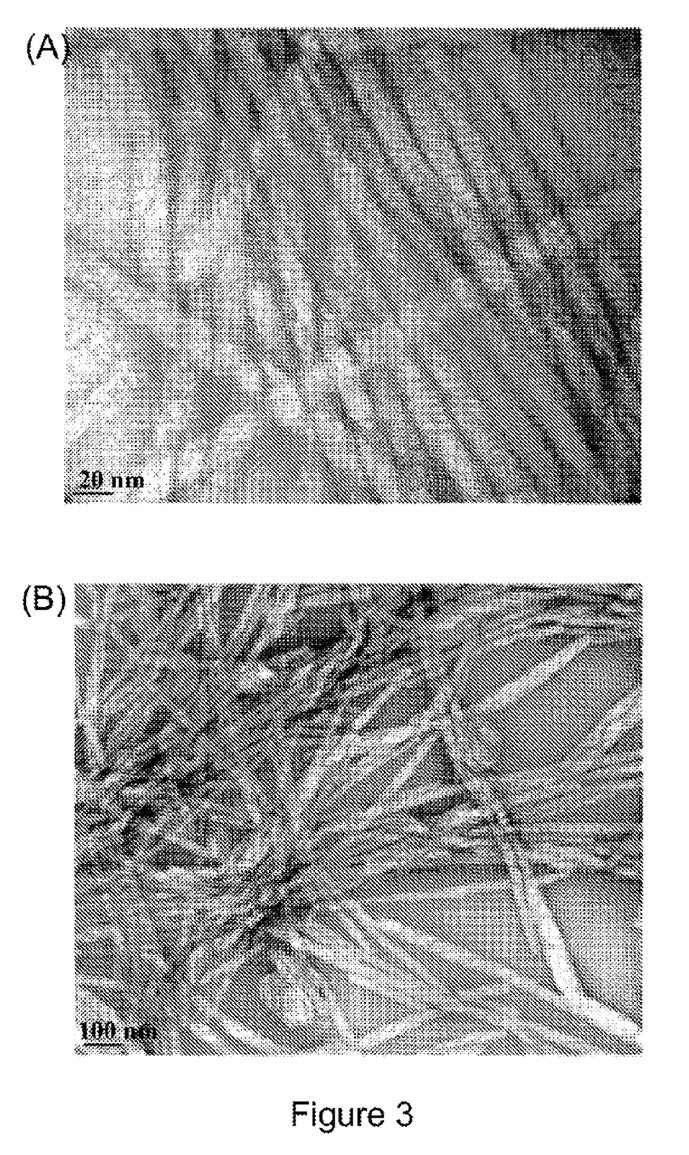
FIG. 3 represents photos taken under a microscope of FGNs without (3A) or with (3B) encapsulated QDs.

Furthermore, FIG. 2 shows the fluorescence spectrum of a solution of encapsulated QDs in water (a) and of the supernatant after the formation of the gel according to the protocol described in this example (b). The capture of the encapsulated QDs by the FGN used was observed under a microscope (FIGS. 3A and 3B).

Conclusion

The FGNs (amphiphilic fluorinated glycosyl nucleosides) make it possible to form a gel on contact with the liquid medium which makes it possible to decontaminate a liquid medium contaminated with particles having a size of less than 20 nm (encapsulated QDs).

Example 2: Decontamination of a Liquid Medium Containing Gold Nanoparticles

In this example, FGNs (amphiphilic fluorinated glycosyl nucleosides) were used as supramolecular system comprising low-molecular-weight molecules for decontaminating a liquid medium comprising gold nanoparticles ("AuNPs").

Material

Amphiphilic Fluorinated Glycosyl Nucleosides (FGNs):

5'-(4-))2H,2H,3H,3H-perfluoroundecanamide)methyl)-1H-1,2,3-triazol-1-yl)N3-)1-((b-D-glucopyranoside)-1H-1,2,3-triazol-4-yl)methyl)thymidine was synthesized according to the protocol described in the document Godeau et al. (Godeau et al., *Tetrahedron Lett.*, 2010, vol. 51, p. 1012-1015 [2]).

Chloroauric acid ("HAuCl$_4$"):

The chloroauric acid was obtained from the company Alfa Aesar (ref No. 36400).

Process for Preparing Gold Nanoparticles Covered with L-Lysine

This process was carried out according to the protocol described in Selvakannan et al. (Selvakannan et al., *Langmuir*, 2003, vol. 19, p. 3545-3549 [5]).

100 ml of aqueous solution of chloroauric acid (HAuCl$_4$) at a concentration of 10$^{-4}$ M were reduced by adding 0.01 g of sodium borohydride (NaBH$_4$) at 20-25° C. so as to produce colloidal gold particles. This procedure results in a change of color of the solution from pale yellow to ruby red. This indicates the formation of gold nanoparticles.

The colloidal gold particles were covered by adding 10 ml of an aqueous solution of lysine at 10$^{-3}$ M to 90 ml of colloidal gold particle solution. The mixture is put aside overnight. This will provide the L-lysine with water-soluble gold-capped nanoparticles. The solution obtained was left to stand overnight in order to form the L-lysine-covered AuNPs.

The mean diameter of the AuNPs not covered with L-lysine was 6.5 nm±0.7 nm.

The concentration of the L-lysine-covered AuNPs was 10$^{-4}$ M.

Experimental Section: Formation of a Gel for Decontaminating a Solution Containing L-Lysine-Covered AuNPs 0.1 mg of FGNs in solution at 0.1% (i.e. 1.0 mg·ml$^{-1}$) was mixed with 2 ml of L-lysine-covered AuNPs in solution in water at a concentration of 10$^{-4}$ M in a 2 ml microtube, at 20-25° C.

A gel was prepared by heating the solution to 80° C. in a water bath with constant agitation until a visually clear solution was obtained. The agitation time in this experiment was 3-4 minutes. The solution was then left in the dark for 48 hours in order for it to be able to stabilize.

After 48 hours, a gel was formed with a liquid supernatant. The presence of the gel and of the supernatant was confirmed by turning the microtube upside down: the gel is maintained in the bottom of the tube, while the supernatant flows in the same way as in example 1.

The liquid supernatant was separated from the gel. A ruby red color was observed in the gel, whereas the supernatant was colorless, thereby confirming that all the L-lysine-covered AuNPs were captured in the FGN gel.

Figure 4:
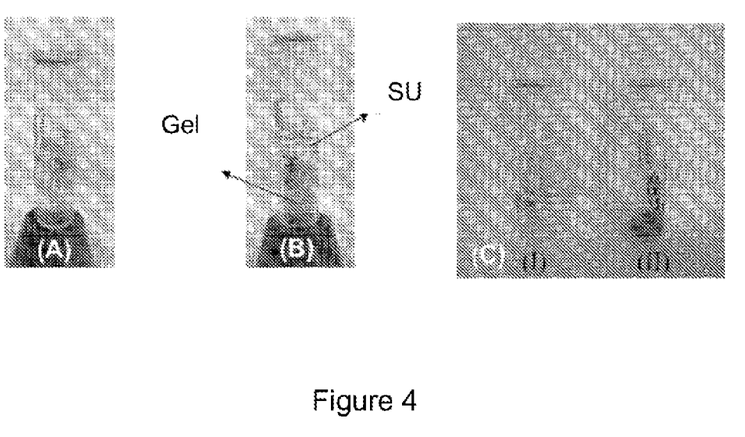
FIG. 4 represents a microtube (a) of a solution of AuNPs covered with L-lysine in water, (b) of AuNPs covered with L-lysine 48 hours after the formation of the hydrogel of FGNs and (c) of the colorless liquid supernatant (I) and of the gel of FGNs and of AuNPs covered with L-lysine of ruby red color (II).

Furthermore, FIG. 4 shows the fluorescence spectrum (a) of a solution of L-lysine-covered AuNPs in water, (b) of the L-lysine-covered AuNPs 48 hours after the formation of the FGN gel, and (c) of the colorless liquid supernatant (I) and of the ruby red-colored gel of FGNs and of L-lysine covered AuNPs.

Conclusion

The FGNs (amphiphilic fluorinated glycosyl nucleosides) make it possible to form a gel on contact with the liquid medium which makes it possible to decontaminate a liquid medium contaminated with L-lysine-covered gold particles having a size of less than approximately 6.5 nm.

Example 3: Decontamination of a Liquid Medium Containing QDs

In this example, natural polymers were used as supramolecular system comprising a polymer for decontaminating a liquid medium comprising encapsulated quantum dots ("QDs").

Material

Jellyfish:

*Mnemiopsis Leidyi* ctenophore jellyfish (Agassiz, 1865) weighing 0.5 gram and 1 centimeter in diameter were harvested from the Etang de Berre [Berre lake] (France).

These jellyfish consist of glycosaminoglycans (GAGs) and/or of mucopolysaccharides.

Scyphozoa Cnidaria:

Scyphozoa Cnidaria, *Aurelia*, weighing 200 g and 10 centimeters in diameter were harvested from the Etang de Berre [Berre lake] (France).

Encapsulated (DOPC/DOTU) Quantum Dots (QDs):

The encapsulated QDs were obtained in the same way as in example 1 above.

The size of the encapsulated QDs obtained is less than or equal to 20 nm (measured on a Zetasizer apparatus by means of DLS experiments) (Binil Itty Ipe et al. [4]).

Their concentration was 17 microg·ml$^{-1}$ in water (measured by fluorescence spectroscopy). The fluorescence spectra were recorded on an LS 55 spectrofluorimeter (Perkin Elmer) equipped with a xenon flashlamp. The data processing was carried out with the SigmaPlot 11 program.

Experimental Section: Formation of a Gel for Decontaminating a Solution Containing Encapsulated QDs About ten *Mnemiopsis* jellyfish were brought into contact with 1 ml of QDs in solution in water at a concentration of 17 μg·ml$^{-1}$ in a 5 ml glass tube, at 20-25° C.

The mixture was moderately agitated for a few seconds and left to stand for 2 to 3 days.

The glass tube containing the above reaction mixture was examined under UV light immediately after mixing. It was observed that, under UV, the entire reaction mixture was fluorescent red, with the exception of the jellyfish portions. The jellyfish portion appeared as black marks and no fluorescence was observed. This means that the encapsulated QDs were absorbed only on the surface of the jellyfish and are not capable of penetrating into the jellyfish.

After 24 hours, the same observations as above were observed. The jellyfish were still alive.

After 48 hours, all the jellyfish were dead and divided into small soft pieces. The entire solution was fluorescent red under UV.

After 72 hours, the entire solution became transparent with some soft pieces precipitated at the bottom of the glass tube or stuck to the surface of the tube. The liquid supernatant was carefully removed and was observed under UV. Surprisingly, no fluorescence was observed. Virtually all the encapsulated QDs were absorbed by the dead jellyfish. When this reaction mixture is filtered through a strip of Whatman paper under gravity, a filtrate with no QD is obtained.

Experiments on *Aurelia aurita* Scyphozoa Cnidaria (Linnaueus, 1758) weighing 200 g and 10 centimeters in diameter also give the same results.

The invention claimed is:

1. A process for subtracting nanoparticles from a liquid medium containing the same, comprising a step
   (a) of adding a supramolecular system to said liquid medium at a temperature of between 2 and 95° C., wherein the supramolecular system comprises:
   at least one low-molecular-weight molecule,
   wherein said low-molecular-weight molecule being of formula (I), said supramolecular system forming a gel on contact with the liquid medium, said gel capturing the nanoparticles contained in said liquid medium, and a step (b) of separating said liquid medium and said gel having captured said nanoparticles, wherein said low-molecular-weight molecule being of formula (I) below:

wherein:
X represents an oxygen atom;
B represents a natural or unnatural puric or pyrimidic base, optionally substituted with an $R_3'$ group as defined below;
substituents $L_1$ and $L_2$:
are identical or different and represent:
(i) a hydrogen atom,
(ii) a hydroxyl group,
(iii) a heteroaryl group comprising 1 to 4 nitrogen atoms, unsubstituted or substituted with a saturated or unsaturated, linear or branched $C_2$-$C_{30}$ hydrocarbon-based chain,
(iv) a group chosen from an oxycarbonyl group —O—C(O)—, a thiocarbamate group —O—C(S)—NH—, a carbonate group —O—C(O)—O—, a carbamate group —O—C(O)—NH—, an ether group —O—, a phosphate group or a phosphonate group, knowing that said $L_1$ group is substituted with an $R_1$ group and said $L_2$ group is substituted with an $R_2$ group, where $R_1$ and $R_2$, which may be identical or different, represent:
a linear or branched, saturated or unsaturated, partially fluorinated or perfluorinated, $C_2$-$C_{30}$, hydrocarbon-based chain,
a $C_2$-$C_{30}$ acyl radical, or
an acylglycerol group,
or
form a ketal group of formula (II) below:

formula (II) in which $K_1$ and $K_2$ are identical or different and represent a saturated or unsaturated $C_1$-$C_{19}$ hydrocarbon-based chain,
$R_3$ and $R_3'$
represent, independently of one another:
(i) a hydroxyl, amino, phosphate, phosphonate, phosphocholine, O-alkyl phosphocholine, thiophosphate or phosphonium group,
(ii) a linear or branched $C_2$-$C_{30}$ alkyl chain optionally substituted with at least one hydroxyl group,
(iii) a —$(CH_2)_n$—V—$R_8$ group, wherein V represents an —O—, —S— or —NH— group, $R_8$ represents a $C_2$-$C_{30}$ alkyl, and n is an integer from 1 to 50,
(iv) a —V—C(O)—$R_8$ group, wherein V represents an —O—, —S— or —NH— group, and $R_8$ represents a $C_2$-$C_{30}$ alkyl,
or
(v) a heteroaryl group containing from 1 to 4 nitrogen atoms, said heteroaryl group being unsubstituted or substituted with a $C_2$-$C_{30}$ alkyl, or with a —$(CH_2)_m$—O—$(CH_2)_p$—$R_9$ group, or with a —$(CH_2)_{0-1}$—Y—C(=O)—R" group, or with a monosaccharide or polysaccharide, or with a group:

or with a group:

wherein:
m is an integer from 1 to 6,
p is an integer from 0 to 10 and
$R_9$ represents a $C_1$ to $C_{10}$ alkyl group, or a cyclic ketal group containing 5 to 7 carbon atoms, said cyclic ketal group being unsubstituted or substituted with at least one linear or branched $C_2$-$C_{30}$ alkyl, a sterol group, a diacyl glycerol, a hydrofluorocarbon-based chain or at least one monosaccharide or polysaccharide,
Y is an oxygen atom, an NH group or a sulfur atom,
and R" is a hydrocarbon-based chain or a fluorocarbon-based chain,
R' is a hydrocarbon-based chain.

2. The process according to claim 1, also comprising, before step (b), when the temperature of the liquid medium obtained in step (a) is below 50° C., the following intermediate steps:
   (a1) heating the medium obtained in step (a) to a temperature of between 50 and 95° C., and
   (a2) cooling the medium obtained in step (a1) to a temperature of between 2 and 50° C.

3. The process according to claim 1, wherein the concentration of supramolecular system used is between 0.001 mg·ml$^{-1}$ and 100 mg·ml$^{-1}$ of aqueous medium.

4. The process according to claim 1, wherein the nanoparticles have a size of between 5 nm and 100 nm.

5. The process according to claim 1, wherein the liquid medium is chosen from the group comprising water, an organic solvent and a polyphase medium.

6. The process according to claim 1, wherein said low-molecular-weight molecule is an amphiphilic fluorinated glycosyl nucleoside.

7. The process according to claim 1, wherein
X represents an oxygen atom, and/or
B represents a thymine, adenine, guanine, cytosine, 6-methoxypurine or hypoxanthine or an unnatural puric or pyrimidic base, which can encompass the base:

wherein:
$R_3'$ is as defined below,
and/or
$L_1$ represents a hydroxyl group, $L_2$ represents a hydrogen atom, or $L_1$ and $L_2$ together form a ketal group of formula (II) below:

(II)

wherein $K_1$ and $K_2$ are identical or different and represent a saturated or unsaturated $C_1$-$C_{19}$ hydrocarbon-based chain
and/or
$R_3$ and $R_3'$
represent:
(i) a hydroxyl, amino, phosphate, phosphonate, phosphocholine, O-alkyl phosphocholine, thiophosphate or phosphonium group,
(ii) a linear or branched $C_2$-$C_{30}$ alkyl chain, optionally substituted with at least one hydroxyl group,
(iii) a —(CH$_2$)$_n$—V—R$_8$ group, wherein V represents an —O—, —S— or —NH— group, $R_8$ represents a $C_2$-$C_{30}$ alkyl, and n is an integer from 1 to 50,
(iv) a —V—C(O)—R$_8$ group, wherein V represents an —O—, —S— or —NH— group, and $R_8$ represents a $C_2$-$C_{30}$ alkyl,
or
(v) a heteroaryl group containing from 1 to 4 nitrogen atoms, said heteroaryl group being unsubstituted or substituted with a $C_2$-$C_{30}$ alkyl, or with a (CH$_2$)$_m$—O—(CH$_2$)$_p$—R$_9$ group, or with a —(CH$_2$)$_{0-1}$—Y—C(=O)—R" group, or with a monosaccharide or polysaccharide, or with a group:

or with a group:

wherein:
m is an integer from 1 to 6,
p is an integer from 0 to 10 and
$R_9$ represents a $C_1$ to $C_{10}$ alkyl group, or a cyclic ketal group containing 5 to 7 carbon atoms, said cyclic ketal group being unsubstituted or substituted with at least one linear or branched $C_2$-$C_{30}$ alkyl, a sterol group, a diacyl glycerol, a hydrofluorocarbon-based chain or at least one monosaccharide or polysaccharide,
Y is an oxygen atom, an NH group or a sulfur atom,
and R" is a hydrocarbon-based chain or a fluorocarbon-based chain,
R' is a hydrocarbon-based chain.

8. The process according to claim 1, wherein:

X represents an oxygen atom,

B represents an unnatural pyrimidic base substituted with a heteroaryl group containing three nitrogen atoms, said heteroaryl group being substituted with a group:

substituents $L_1$ and $L_2$ are identical or different and represent:

(i) a hydrogen atom, (ii) a hydroxyl group, $R_3$ represents a heteroaryl group comprising three nitrogen atoms, said heteroaryl group being substituted with a group:

wherein:

R' is a hydrocarbon-based chain;

Y is an oxygen atom, an NH group or a sulfur atom, and R" is a hydrocarbon-based chain or a fluorocarbon-based chain.

9. The process according to claim 1, wherein

X represents an oxygen atom;

B represents a puric or pyrimidic base;

substituents $L_1$ and $L_2$ form a ketal group of formula (II) below:

(II)

formula (II) in which $K_1$ and $K_2$ are identical or different and represent a saturated or unsaturated $C_1$-$C_{19}$ hydrocarbon-based chain, $R_3$ represents a phosphocholine group.

10. The process according to claim 1, wherein said low-molecular-weight molecule is chosen from:

the group defined by formula (III) below, wherein R' is a hydrocarbon-based chain:

(III)

the group defined by formula (IV) below, wherein Y is an oxygen atom, an NH group or a sulfur atom, and R" is a hydrocarbon-based chain or a fluorocarbon-based chain:

(IV)

the group defined by formula (V) below, wherein n is an integer between 0 and 19:

(V)

or the group defined by formula (VI) below, wherein n is an integer between 0 and 19:

(VI)

11. The process according to claim 1, wherein said low-molecular-weight molecule is chosen from the group comprising:

5'-(4-((2H,2H,3H,3H-perfluoroundecanamide)methyl)-1H-1,2,3-triazol-1-yl)-N3-(1-((β-D-glucopyranoside)-1H-1,2,3,-triazol-4-yl)methyl)thymidine, 5'-(4-((1H, 1H,2H, 2H-perfluoroundecanamide)methyl)-1H-1,2,3-triazol-1-yl)-N3-(1-((β-D-glucopyranoside)-1H-1,2,3-triazol-4-yl)methyl)thymidine, 5'-(4-((oleamide)methyl)-1H-1,2,3-triazol-1-yl)-N3-(1-((β-D-glucopyranoside)-1H-1,2,3-triazol-4-yl)methyl)thymidine, 5'-(4-((stearamide)methyl)-1H-1,2,3-triazol-1-yl)-N3-(1-((β-D-glucopyranoside)-1H-1,2,3-triazol-4-yl)methyl)thymidine, 5'-(4-((octadecyloxy)methyl)-1H-1,2,3-triazol-1-yl)-N3-(1-((β-D-glucopyranoside)-1H-1,2,3-triazol-4-yl)methyl)thymidine, and 5'-(4-((cholesteryloxy)methyl)-1H-1,2,3-triazol-1-yl)-N3-(1-((β-D-glucopyranoside)-1H-1,2,3-triazol-4-yl)methyl)thymidine, 2',3'-O-18-pentatriacontanylidenuridine-5'-phosphocholine, 2',3'-O-18-pentatriacontanylidenadenosine-5'-phosphocholine, and a mixture of at least two of these compounds.

* * * * *